US012797291B2

(12) United States Patent
Paradis

(10) Patent No.: US 12,797,291 B2
(45) Date of Patent: Nov. 17, 2026

(54) METHODS AND DEVICES TO IMPROVE THE EFFICACY OF CARDIOPULMONARY RESUSCITATION

(71) Applicant: Norman Alan Paradis, Putney, VT (US)

(72) Inventor: Norman Alan Paradis, Putney, VT (US)

( * ) Notice: Subject to any disclaimer, the term of this patent is extended or adjusted under 35 U.S.C. 154(b) by 1088 days.

(21) Appl. No.: 17/850,664

(22) Filed: Jun. 27, 2022

(65) Prior Publication Data

US 2023/0000719 A1 Jan. 5, 2023

Related U.S. Application Data

(60) Provisional application No. 63/215,262, filed on Jun. 25, 2021.

(51) Int. Cl.

| | |
|---|---|
| ***A61H 31/00*** | (2006.01) |
| ***A61B 6/12*** | (2006.01) |
| ***A61H 9/00*** | (2006.01) |
| ***A61M 5/00*** | (2006.01) |
| ***A61M 60/13*** | (2021.01) |
| ***A61M 60/295*** | (2021.01) |
| ***A61M 60/867*** | (2021.01) |
| *A61M 25/01* | (2006.01) |

(52) U.S. Cl.

CPC ............. *A61H 31/006* (2013.01); *A61B 6/12* (2013.01); *A61H 9/0092* (2013.01); *A61H 31/008* (2013.01); *A61M 5/007* (2013.01); *A61M 60/13* (2021.01); *A61M 60/295* (2021.01); *A61M 60/867* (2021.01); *A61H 2201/10* (2013.01); *A61H 2230/045* (2013.01); *A61M 2025/0166* (2013.01)

(58) Field of Classification Search

CPC .................................................... A61H 31/006

See application file for complete search history.

(56) References Cited

U.S. PATENT DOCUMENTS

| | | | |
|---|---|---|---|
| 2,699,163 | A | 1/1955 | Engstrom |
| 2,899,955 | A | 8/1959 | Huxley, III et al. |
| 3,364,924 | A | 1/1968 | Barkalow |

(Continued)

FOREIGN PATENT DOCUMENTS

| | | | |
|---|---|---|---|
| EP | 2709581 | B1 | 7/2017 |
| EP | 3431069 | A1 | 1/2019 |

(Continued)

OTHER PUBLICATIONS

Abella, Benjamin S. et al., CPR quality improvement during in-hospital cardiac arrest using a real-time audiovisual feedback system, Resuscitation, 2007, 73, pp. 54-61.

(Continued)

*Primary Examiner* — Joseph M Santos Rodriguez

(74) *Attorney, Agent, or Firm* — Nathaniel A. Wickliffe

(57) ABSTRACT

A system and method for integrating and synchronizing an automated mechanical cardiopulmonary resuscitation (CPR) device with components of cardiac catheterization laboratories so as to enhance the efficacy of each intervention. Synchronization can include image gating so that a monitor shows real time images during relaxation of the CPR, and a static image during compression of the CPR.

1 Claim, 4 Drawing Sheets

(56) References Cited

U.S. PATENT DOCUMENTS

| | | | |
|---|---|---|---|
| 3,481,327 | A | 12/1969 | Drennen |
| 3,683,655 | A | 8/1972 | White et al. |
| 4,198,963 | A | 4/1980 | Barkalow et al. |
| 4,349,015 | A | 9/1982 | Alferness |
| 4,397,306 | A | 8/1983 | Weisfeldt et al. |
| 4,424,806 | A | 1/1984 | Newman et al. |
| 4,664,098 | A | 5/1987 | Woudenberg et al. |
| 4,770,164 | A | 9/1988 | Lach et al. |
| 4,838,263 | A | 6/1989 | Warwick et al. |
| 4,840,167 | A | 6/1989 | Olsson et al. |
| 4,928,674 | A | 5/1990 | Halperin et al. |
| 5,076,259 | A | 12/1991 | Hayek |
| 5,078,134 | A | 1/1992 | Heilman et al. |
| 5,222,478 | A | 6/1993 | Scarberry et al. |
| 5,454,779 | A | 10/1995 | Lurie et al. |
| 5,490,820 | A | 2/1996 | Schock et al. |
| 5,496,257 | A | 3/1996 | Kelly |
| 5,743,864 | A | 4/1998 | Baldwin, II |
| 5,769,800 | A | 6/1998 | Gelfand et al. |
| 6,171,267 | B1 | 1/2001 | Baldwin, II |
| 6,174,295 | B1 | 1/2001 | Cantrell et al. |
| 6,213,960 | B1 | 4/2001 | Sherman et al. |
| 6,224,562 | B1 | 5/2001 | Lurie et al. |
| 6,374,827 | B1 | 4/2002 | Bowden et al. |
| 6,390,996 | B1 | 5/2002 | Halperin et al. |
| 6,393,316 | B1 | 5/2002 | Gillberg et al. |
| 6,418,342 | B1 | 7/2002 | Owen et al. |
| 6,427,685 | B1 | 8/2002 | Ray |
| 6,752,771 | B2 | 6/2004 | Rothman et al. |
| 6,827,695 | B2 | 12/2004 | Palazzolo et al. |
| 6,869,409 | B2 | 3/2005 | Rothman et al. |
| 7,032,596 | B2 | 4/2006 | Thompson et al. |
| 7,220,235 | B2 | 5/2007 | Geheb et al. |
| 8,433,412 | B1 | 4/2013 | Westlund et al. |
| 8,478,401 | B2 | 7/2013 | Freeman |
| 8,795,208 | B2 | 8/2014 | Walker |
| 9,474,892 | B2 | 10/2016 | Chang et al. |
| 10,245,209 | B2 | 4/2019 | Lurie et al. |
| 10,772,793 | B2 | 9/2020 | Paradis |
| 10,888,493 | B2 | 1/2021 | Freeman et al. |
| 10,918,354 | B2 | 2/2021 | Nichol et al. |
| 11,097,118 | B2 | 8/2021 | Freeman et al. |
| 11,253,713 | B2 | 2/2022 | Paradis |
| 11,679,059 | B2 | 6/2023 | Paradis |
| 11,684,542 | B2 | 6/2023 | Paradis |
| 11,744,772 | B2 | 9/2023 | Fabian et al. |
| 2001/0007928 | A1 | 7/2001 | Hansen |
| 2002/0026131 | A1 | 2/2002 | Halperin |
| 2003/0004445 | A1 | 1/2003 | Hall et al. |
| 2004/0162510 | A1 | 8/2004 | Jayne et al. |
| 2004/0230140 | A1 | 11/2004 | Steen |
| 2006/0089574 | A1 | 4/2006 | Paradis |
| 2007/0010765 | A1 | 1/2007 | Rothman et al. |
| 2007/0032829 | A1 | 2/2007 | Ostroff |
| 2007/0060785 | A1 | 3/2007 | Freeman et al. |
| 2007/0225623 | A1 | 9/2007 | Freeman |
| 2007/0299473 | A1 | 12/2007 | Matos |
| 2008/0097534 | A1 | 4/2008 | Myklebust et al. |
| 2008/0275371 | A1 | 11/2008 | Hoffmann |
| 2009/0062701 | A1 | 3/2009 | Yannopoulos et al. |
| 2010/0004572 | A1 | 1/2010 | King |
| 2012/0016179 | A1 | 1/2012 | Paradis et al. |
| 2012/0116272 | A1 | 5/2012 | Hampton et al. |
| 2012/0146797 | A1 | 6/2012 | Oskin et al. |
| 2013/0072830 | A1* | 3/2013 | Illindala ............... A61H 31/006 601/41 |
| 2014/0094724 | A1 | 4/2014 | Freeman |
| 2014/0155792 | A1 | 6/2014 | Karve et al. |
| 2014/0213942 | A1 | 7/2014 | Hanson |
| 2014/0336546 | A1 | 11/2014 | Chapman et al. |
| 2014/0358047 | A1 | 12/2014 | Lurie |
| 2015/0094624 | A1 | 4/2015 | Illindala |
| 2015/0265497 | A1 | 9/2015 | Kaufman et al. |
| 2016/0317385 | A1 | 11/2016 | Salcido et al. |
| 2016/0361228 | A1 | 12/2016 | Paradis et al. |
| 2017/0035650 | A1 | 2/2017 | Taylor et al. |
| 2017/0105898 | A1 | 4/2017 | Taylor et al. |
| 2017/0266078 | A1 | 9/2017 | Jayne et al. |
| 2018/0021216 | A1 | 1/2018 | Paradis et al. |
| 2018/0161225 | A1* | 6/2018 | Zerhusen ............... A47C 27/10 |
| 2018/0168922 | A1 | 6/2018 | Chapman et al. |
| 2018/0325771 | A1* | 11/2018 | Freeman .............. A61H 31/005 |
| 2019/0091099 | A1 | 3/2019 | Nilsson et al. |
| 2019/0117501 | A1 | 4/2019 | Chapman et al. |
| 2019/0209428 | A1 | 7/2019 | Paradis |
| 2019/0357778 | A1* | 11/2019 | Wilson ................. A61M 5/145 |
| 2020/0155862 | A1 | 5/2020 | Paradis |

FOREIGN PATENT DOCUMENTS

| | | | |
|---|---|---|---|
| KR | 101383051 | B | 4/2014 |
| KR | 20160146462 | A | 12/2016 |
| WO | 9628128 | A1 | 9/1996 |
| WO | 9965560 | A2 | 12/1999 |
| WO | 2010099628 | A1 | 9/2010 |
| WO | 2014051934 | A1 | 4/2014 |
| WO | 2015048347 | A1 | 4/2015 |
| WO | 2020018728 | A1 | 1/2020 |

OTHER PUBLICATIONS

Aiello et al., "Real-time ventricular fibrillation amplitude-spectral area analysis to guide timing of shock delivery improves defibrillation efficacy during cardiopulmonary resuscitation in swine", Journal of the American Heart Association, DOI: 10.1161/JAHA.117.006749, pp. 1-15.

Arntz, H.R., et al. Phased Chest and Abdominal Compression-Decompression Versus Conventional Cardiopulmonary Resuscitation in Out-of-Hospital Cardiac Arrest, American Heart Association, Inc., Aug. 14, 2001, pp. 768-772.

Aufderheide, T. P., et al. "Clinical evaluation of an inspiratory impedance threshold device during standard cardiopulmonary resuscitation in patients with out-of-hospital cardiac arrest." Crit Care Med. 33.4 (2005): 734-40.

Babbs, MD, Charles F., Preclinical Studies of Abdominal Counterpulsation in CPR, Annals of Emergency Medicine, 13: Sep. 9, 1984, pp. 761-763.

Barkalow, B. H. "Comparison of miniaturized pneumatic chest compressor to Thumper." Resuscitation 79.3 (2008): 509.

Beck, C. S., E. C. Weckesser, and F. M. Barry. 1956. 'Fatal heart attack and successful defibrillation; new concepts in coronary artery disease', J Am Med Assoc, 161: 434-6.

Berkowitz, Ivor D., et al., Blood Flow during Cardiopulmonary Resuscitation with Simultaneous Compression and Ventilation in Infant Pigs, Pediatric Research, 1989, vol. 26, No. 6, pp. 558-564.

Bircher, N., et al, Do Intrathoracic Pressure Fluctuation or Heart Compressions Move Blood During External Cardiopulmonary Resuscitation (CPR)?, Resuscitation Research Center and the Department of Anesthesiology, University of Pittsburgh, ASA Abstract, V53, No. 3, Sep. 1980.

Cabanas, J. G., J. B. Myers, J. G. Williams, V. J. De Maio, and M. W. Bachman. 2015. 'Double Sequential External Defibrillation in Out-of-Hospital Refractory Ventricular Fibrillation: A Report of Ten Cases', Prehosp Emerg Care, 19: 126-30.

Callaway, Clifton W.; Why We Should No Longer Terminate Resuscitations after 20 Minutes; Mar. 2, 2016; Journal of Emergency Medical Services; vol. 41, Issue 3; (Year: 2016).

Cave DM, Gazmuri RJ, Otto CW et al. "Part 7: CPR techniques and devices: 2010 American Heart Association Guidelines for Cardiopulmonary Resuscitation and Emergency Cardiovascular Care". Circ 2010; 122(18 Suppl 3): S720-S728.

Chan PS, McNally B, Tang F, Kellermann A. "Recent trends in survival from out-of-hospital cardiac arrest in the United States" Circ 2014; 130(21):1876-1882.

Cohen, Todd J., et al., Active Compression-Decompression Resuscitation: A Novel Method of Cardiopulmonary Resuscitation, American Heart Journal, Nov. 1992, pp. 1145-1150.

(56) References Cited

OTHER PUBLICATIONS

Cohen, Todd J., et al., Active Compression-Decompression, A New Method of Cardiopulmonary Resuscitation, JAMA, Jun. 3, 1992, vol. 267, No. 21, pp. 2916-2923.
Deakin, C. D., R. M. McLaren, G. W. Petley, F. Clewlow, and M. J. Dalrymple-Hay. 1998. 'Effects of positive end-expiratory pressure on transthoracic impedance—implications for defibrillation', Resuscitation, 37: 9-12.
Esibov A, Banville I, Chapman FW, Boomars R, Box M, Rubertsson S. "Mechanical chest compressions improved aspects of CPR in the LINC trial". Resuscitation 2015; 91:116-121.
Ewy, G.A., D.A. Hellman, S. McClung, and D. Taren. 1980. 'Influence of ventilation phase on transthoracic impedance and defibrillation effectiveness', Crit. Care Med, 8: 164-66.
Haas, Thorsten, et al, Revisiting the cardiac versus thoracic pump mechanism during cardiopulmonary resuscitation, Resuscitation, 58, Nov. 5, 2002, pp. 113-116.
Hallstrom A, Rea TD, Sayre MR et al. "Manual chest compression vs use of an automated chest compression device during resuscitation following out-of-hospital cardiac arrest: a randomized trial". JAMA 2006; 295(22):2620-2628.
Halperin, H. R., et al. "Cardiopulmonary resuscitation with a novel chest compression device in a porcine model of cardiac arrest: improved hemodynamics and mechanisms." J.Am.Coll.Cardiol. 44.11 (2004): 2214-20.
Halperin, M.D., Henry R., A Preliminary Study of Cardiopulmonary Resuscitation by Circumferential Compression of the Chest with use of a Pneumatic Vest, The New England Journal of Medicine, vol. 329 No. 11, Sep. 9, 1993, pp. 762-768.
Hostler D, Everson-Stewart S, Rea TD et al. "Effect of real-time feedback during cardiopulmonary resuscitation outside hospital: prospective, cluster-randomised trial". BMJ 2011; 342:d512.
Jenkins, Constance, et al, Effects of the ResQPOD on Kinetics, Hemodynamics of Vasopressin, and Survivability in a Porcine Cardiac Arrest Model, Military Medicine, vol. 180, Sep. 2015, pp. 1011-1016.
Kerber, R. E., J. D. Bourland, M. J. Kallok, P. Hite, B. Pritchard, F. Charbonnier, C. Birkett, K. Fox-Eastham, and R. A. Kieso. 1990. 'Transthoracic defibrillation using sequential and simultaneous dual shock pathways: experimental studies', Pacing Clin Electrophysiol, 13: 207-17.
Kerber, R. E., J. Grayzel, R. Hoyt, M. Marcus, and J. Kennedy. 1981. 'Transthoracic resistance in human defibrillation. Influence of body weight, chest size, serial shocks, paddle size and paddle contact pressure', Circulation, 63: 676-82.
Kerber, R.E., K.T. Spencer, M.J. Kallok, C. Birkett, R. Smith, D. Yoerger, and R.A. Kieso. 1994. 'Overlapping sequential pulses. A new waveform for transthoracic defibrillation', Circ, 89: 2369-79.
Kirchhof, P., L. Eckardt, P. Loh, K. Weber, R. J. Fischer, K. H. Seidl, D. Bocker, G. Breithardt, W. Haverkamp, and M. Borggrefe. 2002. 'Anterior-posterior versus anterior-lateral electrode positions for external cardioversion of atrial fibrillation: a randomised trial', Lancet, 360: 1275-9.
Kleinman, Monica E., et al, Part 5: Adult Basic Life Support and Cardiopulmonary Resuscitation Quality: 2015 American Heart Association Guidelines Update for Cardiopulmonary Resuscitation, and Emergency Cardiovascular Care, Circulation, 2015, 132, S414-S435.
Kouwenhoven, Jude; Knickerbocker, Cardiac Arrest—The Science and Practice of Resuscitation Medicine, (19600000), p. 96.
Kouwenhoven, W.B Closed-Chest Cardiac Massage, JAMA, Jul. 9, 1960, vol. 173, No. 10, pp. 1064-1067.
Lafuente-Lafuente et al., "Active chest compression-decompression for cardiopulmonary resuscitation (Review)," The Cochrane Collaboration, 2009, Issue 3 (40 pages).
Li, Y., H. Wang, J. H. Cho, W. Quan, G. Freeman, J. Bisera, M. H. Weil, and W. Tang. 2010. 'Defibrillation delivered during the upstroke phase of manual chest compression improves shock success', Crit Care Med, 38: 910-5.
Liao et al., "Manual versus mechanical cardiopulmonary resuscitation. An experimental study in pigs", BMC Cardiovascular Disorders, Oct. 2010, 10:53, http://www.biomedcentral.com/1471-2261/10/53 (8 pages).
Lurie et a., "Improving active compression-decompression resuscitation with an inspiratory impedance valve", originally published Mar. 15, 1995, https://doi.org/10.1161/01.CIR.91.6.1629, Circulation. 1995; 91:1629-1632.
Lurie et al., "Improving standard cardiopulmonary resuscitation with an inspiratory impedance threshold valve in a porcine model of cardiac arrest", Anesth Analg 2001; 93:649-655.
Lurie, K.G., Improving active compression-decompression cardiopulmonary resuscitation with an inspiratory impedance value, Abstract Circulation 1995; 91/6 (1 page abstract).
McClung, Christian D., et al.; Interposed Abdominal Compression CPR for an Out-of-Hospital Cardiac Arrest Victim Failing Traditional CPR; Oct. 20, 2015; Western Journal of Emergency Medicine; vol. XVI, No. 5; 690-692 (Year: 2015).
McDonald, M.D., John L, Systolic and Mean Arterial Pressures During Manual and Mechanical CPR in Humans, Annals of Emergency Medicine, 11:Jun. 6, 1982, pp. 292-295.
Michael, John R., et al., Mechanisms by with epinephrine augments cerebral and myocardial perfusion during cardiopulmonary resuscitation in dogs, Circulation 69, No. 4, 822-834, 1984.
Neumann T, Gruenewald M, Lauenstein C, Drews T, Iden T, Meybohm P. "Hands-on defibrillation has the potential to improve the quality of cardiopulmonary resuscitation and is safe for rescuers—a preclinical study". J Am Heart Assoc 2012; 1(5):e001313.
Niemann Md., James T., Cough-CPR, Documentation of systemic perfusion in man and in an experimental model: a window to the mechanism of blood flow in external CPR, Critical Care Medicine, vol. 8, No. 3, pp. 141-146, Mar. 1980.
Ong ME, Annathurai A, Shahidah A et al. "Cardiopulmonary resuscitation interruptions with use of a load-distributing band device during emergency department cardiac arrest". Ann Emerg Med 2010; 56(3):233-241.
Ong, M. E., et al. "Use of an automated, load-distributing band chest compression device for out-of-hospital cardiac arrest resuscitation." JAMA 295.22 (2006): 2629-37.
Paradis M.D., Norman A., Simultaneous Aortic, Jugular Bulb, and Right Atrial Pressures During Cardiopulmonary Resuscitation in Humans, Insights Into Mechanisms, Circulation, vol. 80, No. 2, Aug. 1989.
Paradis, N. A. "Is this the next step for CPR?" Am. J. Emerg. Med. 18 34.1 (2016): 97-99.
Paradis, N. A., et al. "Coronary perfusion pressure during external chest compression in pseudo-EMD, comparison of systolic versus diastolic synchronization." Resuscitation 83.10 (2012): 1287-91.
Paradis, Norman A., et al, Cardiac Arrest, The Science and Practice of Resuscitation Medicine, 2nd edition, Cambridge University Press 2007.
Plaisance et al., "Evaluation of an impedance threshold device in patients receiving active compression-decompression cardiopulmonary resuscitation for out of hospital cardiac arrest", Elsevier, Resuscitation 61 (2004) 265-271, www.elsevier.com/locate/resuscitation.
Plaisance P, Lurie KG, Payen D. "Inspiratory impedance during active compression-decompression cardiopulmonary resuscitation: a randomized evaluation in patients in cardiac arrest". Circ 2000; 101(9):989-994.
Plaisance, M.D., Patrick, A Comparison of Standard Cardiopulmonary Resuscitation and Active Compression-Decompression Resuscitation for Out-of-Hospital Cardiac Arrest, New England Journal of Medicine, vol. 341, No. 8, Aug. 19, 1999, pp. 569-575.
Plaisance, P., et al. "Use of an inspiratory impedance threshold device on a facemask and endotracheal tube to reduce intrathoracic pressures during the decompression phase of active compression-decompression cardiopulmonary resuscitation." Crit Care Med. 33.5 (2005): 990-94.
Qvigstad et al., "Clinical pilot study of different hand positions during manual chest compressions monitored with capnography", Resuscitation 84 (2013) 1203-1207, www.elsevier.com/locate/resuscitation.

(56) References Cited

OTHER PUBLICATIONS

Ralston, Sandra H., Cardiopulmonary Resuscitation with Interposed Abdominal Compression in Dogs, Anesthesia and Analgesia, vol. 61, No. 8, Aug. 1982, pp. 645-651.
Ramirez et al., "Effect of Applying Force to Self-Adhesive Electrodes on Transthoracic Impedance: Implications for Electrical Cardioversion", PACE, vol. 39, Oct. 2016, pp. 1141-1147.
Rubertsson S, Lindgren E, Smekal D et al. "Mechanical chest compressions and simultaneous defibrillation vs conventional cardiopulmonary resuscitation in out-of-hospital cardiac arrest: the LINC randomized trial". JAMA 2014; 311(1):53-61.
Rudikoff, M. T., et al. "Mechanisms of Blood Flow During Cardiopulmonary Resuscitation." Circulation 61 (1980):345-52.
Sanders AB, Kern KB, Ewy GA, Atlas M, Bailey L. "Improved resuscitation from cardiac arrest with open-chest massage". Ann Emerg Med 1984; 13(9 Pt 1):672-675.
Sanders, A.B., K.B. Kern, C.W. Otto, M.M. Milander, and G.A. Ewy. 1989. 'End-tidal carbon dioxide monitoring during cardiopulmonary resuscitation. A prognostic indicator for survival.', JAMA, 262: 1347-51.
Segal, M.D., PhD, Nicolas, Intermittent Positive-Pressure Ventilation, Chest Compression Synchronized Ventilation, Bilevel Ventilation, Continuous Chest Compression, Active Compression Decompression, and Impedance Threshold Device—The Complexity of Ventilation During Cardiopulmonary Resuscitation, Critical Care Medicine, Feb. 2014, vol. 42, No. 2, pp. 480-481.
Shinar Z, Bellezzo J, Paradis N et al. "Emergency department initiation of cardiopulmonary bypass: a case report and review of the literature". J Emerg Med 2012; 43(1):83-86.
Stephenson HE, Corsan Reed L, Hinton JW. "Some Common Denominators in 1200 cases of cardiac arrest". Ann Surg 1953; 137:731-744.
Stiell IG, Nichol G, Leroux BG et al. "Early versus later rhythm analysis in patients with out-of-hospital cardiac arrest". N Engl J Med 2011; 365(9):787-797.
Vector Definition; 2020; Merriam-Webster; https://www.merriam-webster.com/dictionary/vector (Year: 2020).
Voorhees, PhD, William D. et al, Improved Oxygen Delivery During Cardiopulmonary Resuscitation with Interposed Abdominal Compressions, Annals of Emergency Medicine, 12:Mar. 3, 1983, pp. 128-135.
Wang, M.D., Chih-Hung, et al, Active Compression-Decompression Resuscitation and Impedance Threshold Device for Out-of-Hospital Cardiac Arrest: A Systematic Review and Metaanalysis of Randomized Controlled Trials, Critical Sare Medicine, Apr. 2015, vol. 43, No. 4, pp. 889-896.
Weisfeldt, M.D., M.L., et al, Increased intrathoracic pressure—no direct heart compression—causes the rise in intrathoracic vascular pressures during CPR in dogs and pigs, Critical Care Medicine, pp. 377-378, May 1981.
Wik L, Olsen JA, Persse D et al. "Manual vs. integrated automatic load-distributing band CPR with equal survival after out of hospital cardiac arrest. The randomized CIRC trial". Resuscitation 2014; 85(6):741-748.
Wolcke, Md., Benno G., et al, Comparison of Standard Cardiopulmonary Resuscitation Versus the Combination of Active Compression-Decompression Cardiopulmonary Resuscitation and an Inspiratory Impedance Threshold Device for Out-of-Hospital Cardiac Arrest, Circulation, 2003, pp. 108, 2201-2205.
Xie, Z., Q. Yang, M. Li, Z. Huang, Y. Wang, Q. Ling, W. Tang, and Z. Yang. 2018. 'Amplitude screening improves performance of AMSA method for predicting success of defibrillation in swine model', Am J Emerg Med.
Yang, Z., et al. A tourniquet assisted cardiopulmonary resuscitation augments myocardial perfusion in a porcine model of cardiac arrest, Resuscitation 86 (2015) 49-53.
Yeung, J., et al, The use of CPR feedback/prompt devices during training and CPR performance: A systematic review, Resuscitation, 80, pp. 743-751, 2009.
Zoll, P. M., A. J. Linenthal, W. Gibson, M. H. Paul, and L. R. Norman. 1956. 'Termination of ventricular fibrillation in man by externally applied electric countershock', N Engl J Med, 254: 727-32.

* cited by examiner

METHODS AND DEVICES TO IMPROVE THE EFFICACY OF CARDIOPULMONARY RESUSCITATION

RELATED APPLICATIONS

This application claims the benefit of U.S. Provisional Application Ser. No. 63/215,262, filed Jun. 25, 2021, entitled METHODS AND DEVICES TO IMPROVE THE EFFICACY OF MECHANICAL CARDIOPULMINARY RESUSCITATION, the entire disclosure of which is herein incorporated by reference.

FILED OF THE INVENTION

This application relates to cardiopulmonary resuscitation (CPR), and more particularly, to improved mechanical systems and methods for providing efficacious CPR on a patient undergoing treatment in a catheterization laboratory.

BACKGROUND OF THE INVENTION

Cardiovascular disease is among the greatest causes of mortality and morbidity. Once disease of the myocardium or its vasculature exists, procedures may be required for diagnosis and treatment. Cardiac catheterization is among the most common of the invasive cardiac procedures. It is the set of procedures whereby diagnostic and therapeutic catheters are placed within the coronary vasculature or chambers of the heart so as to allow diagnostic and therapeutic interventions. When coronary artery procedures are performed using catheters advanced through arteries and veins from the skin, the procedure is often called percutaneous coronary interventions (PCI). Cardiac catheterization is generally performed in specialized facilities called cardiac catheterization laboratories, also referred to as cathlabs.

Cathlab associated procedures can include angioplasty, percutaneous coronary intervention (PCI), angiography, transcatheter aortic valve replacement, and various other procedures that will be known to those skilled in the art. FIG. 1 is a perspective view of a typical Cathlab showing various components, according to an illustrative embodiment. The major components of the cathlab 100 can include, among others:

- A table 102 for the patient that can be mechanized to allow movement of the patient in the imaging system, and can maintain the patient in the supine position for standardization of imaging and access to the appropriate blood vessels.
- An imaging system 104 that can be fluoroscopy, and can be either monoplane or biplane. The imaging system is often a "C-arm" device with x-ray emitter and detector above and below the patient.
- A monitor display 106 for presentation of fluoroscopic images in real time and delayed retention of images.
- A radiocontrast injector pump 108 for controlled injection of radiocontrast material.
- Additional devices that are often available but not commonly used can include: monitor-defibrillators, standard automated CPR devices, aortic balloon pumps, and left ventricular assist devices.

Use of Radiocontrast in the Cathlab

Radiocontrast agents are used in coronary interventions and angiographies to accentuate vascular structures during fluoroscopy. These contrast agents typically contain iodine as the radiopaque constituent, and can be either ionic or non-ionic in nature, depending on the carrier used for iodine.

Maximization of the contrast injection method can help in obtaining images in which the coronary blood vessels are emphasized and artifacts are minimized. Factors such as: location of injection, concentration, shape, timing, rate, and composition of the contrast bolus can contribute to effectiveness of the contrast medium. In the injection process, one factor is the site, i.e. the blood vessel, chosen to inject the contrast. Faster injection rates allow coronary arteries to be accentuated more and within lesser time i.e. the peak enhancement time for coronary arteries is reduced.

One injection enhancement approach is based on the pattern of radiocontrast administration i.e. it involves a multi-stage injection process with separate doses of contrast, saline, or diluted contrast. Multi-headed injectors that store the radiocontrast and saline solution separately have made this possible. In the biphasic technique a bolus of undiluted radiocontrast is injected first, which is then followed by a smaller volume of saline "chaser." A triphasic approach also may be employed where the undiluted contrast bolus is injected first, followed by a diluted bolus of contrast and finally saline. Using a saline chaser following a contrast bolus ensures that the entire volume of contrast is delivered to the coronary vessels rather than being stuck in the catheter. It can improve coronary angiography by removing the streak artifacts in the images of the coronary artery that are caused by accumulation of contrast in the right ventricle or superior vena cava.

CPR and Motion Artifact

A cathlab can allow a patient to be examined with diagnostic imaging equipment, so that doctors and/or other medical professionals can see the arteries, veins, and chambers of the heart in action while the patient's heart is pumping blood through the circulatory system. The cath lab can be used to monitor the function of a patient's heart, and/or can be used to monitor a patient with various abnormalities or dysfunction in the circulatory system. In some situations, a patient who is undergoing examination in a cath lab may also require the use of cardiopulmonary resuscitation (CPR).

Cardiac arrest can occur in the cath lab, and is associated with dramatically worsened patient outcomes. Historically, when automated CPR devices are used in a cath lab, they are stand-alone devices and not integrated into the imaging systems of the cath lab. When automated CPR devices are used in the cath lab, the chest compressions of CPR can cause motion of visceral structures, including the coronary arteries. Motion of the coronary arteries can cause motion artifact and makes various procedures done in the cath lab more difficult to accomplish accurately and safely. These procedures can include angioplasty, percutaneous coronary intervention (PCI), angiography, transcatheter aortic valve replacement, and various other procedures done in a cath lab that will be known to those skilled in the art.

Motion artifact is a problem in almost all forms of medical imaging, and can interfere with the quality of images during cathlab procedures. Recent approaches have tested deep learning techniques for the removal of motion artifacts through extraction of features and by applying image processing techniques. Convolutional Neural Networks (CNN), in particular, single-scaled and de-noised, CNN have been used.

The vast majority of PCI's are performed in patients with a beating heart under mild sedation. Occasionally, however, cardiac arrest occurs and the procedure must be performed simultaneously with CPR. This circumstance is associated with dramatically worse patient outcomes.

Continuing with PCI in arrested patients without CPR places the patients at much greater risk of poor outcomes. The human brain is intolerant of even short intervals of absent blood flow and ischemia related vital organ injury may result in post-anoxic encephalopathy. Generally, the chest compressions of CPR are started immediately while alternatives such as automated CPR devices, endovascular pumps, or extracorporeal circulation are considered.

Manual CPR and piston based automated CPR devices create blood flow by compressing the anterior chest. This provides motive force to cardiac and thoracic CPR pump mechanisms. However, its application is also associated damage to skeletal and visceral organ structures, and of particular importance in relation to the fluoroscopic imaging utilized in cardiac catheterization, the sternal compressions of CPR create large abnormal motions of cardiac structures. These motion artifacts make fluoroscopic interpretation of coronary anatomy and the phenomena of PCI difficult, which can significantly impede successful performance of PCI procedures. If the coronary artery with the culprit coronary occlusion cannot be successfully reopened by balloon angioplasty and maintained open by stenting, then reversal of the cardiac arrest may be impaired. CPR related motion artifact is particularly challenging for interventional cardiologists because they encounter it only infrequently and do not develop expertise at ignoring it.

Most commonly, when cardiac arrest occurs in the cathlab, cardiopulmonary resuscitation is performed manually with a member of the cathlab team pushing on the middle of the chest. This has a number of limitations, including:

- Manual CPR is generally associated with inadequate forward blood flow.
- The provider of chest compressions is in a suboptimal position and often requires a stepstool to achieve appropriate height above the patient.
- The provider of chest compressions is on the opposite side of the catheterization table, and is often interfering with views of the procedure.
- The hands of the provider of chest compressions are in the fluoroscopic field-of-view. This interferes with imaging and exposes the provider of CPR to x-rays.
- The sternal compressions cause an abnormal anterior-posterior motion of the myocardium which interferes with the cardiologist ability to see the coronary anatomy and the PCI catheter and site.
- The sternal compression of manual CPR are associated with a high rate of skeletal and visceral organ injury. This can potentially be a major threat in anticoagulated PCI patients.

Automated mechanical CPR machines also exist and may be used in the Cathlab instead of manually applied CPR. Historically, when current automated CPR devices are used in a cathlabs, they are stand-alone devices not integrated with the other cathlab devices. This is associated with a number of problems:

- The historical automated CPR machines cannot be pre-placed because of their backboards and arches. This results in a delay in their application.
- Their radiopaque components interfere with imaging.
- Their sternal piston mechanisms apply force to only a small area of the chest and are associated with high rates of skeletal and visceral organ injury. This can potentially be a major threat in anticoagulated PCI patients.
- Similar to manual CPR, the sternal compressions cause an abnormal anterior-posterior motion of the myocardium which interferes with the cardiologist's ability to see the coronary anatomy and the PCI catheter and site.
- These devices tend to move in relation to the patient, resulting in precordial compressions that may wander from the desired location near the mid sternum. This is associated with a loss of efficacy and additional fractures.
- During application these devices tend to become entangled in the sterile drapes placed around the patient.
- When automated CPR devices are used in the cathlab, the chest compressions of CPR can cause motion of visceral structures, including the coronary arteries. Motion of the coronary arteries makes PCI more difficult to accomplish accurately and safely.
- Existing automated CPR devices can interfere with some standard fluoroscopic views of the heart. Some devices interfere with imaging to a degree most cardiologist consider harmful, or unacceptable for effective treatment.
- Some existing automated CPR devices cannot be used in cathlabs with biplane imaging.
- Some existing CPR devices can also have thick backboards that can be very uncomfortable if placed under high-risk patients before any procedures begin. The backboards can also make the devices inconvenient to pre-place or initiate use of in emergency situations.
- Existing automated CPR devices are currently not integrated with the other components of the cathlab system. Thus the performance of CPR cannot be integrated with other therapeutic modalities so as to achieve optimal efficacy.
- The mechanized table that the patient lies upon in cardiac catheterization laboratories are structurally in adequate to the forces applied during CPR. The table will tend to move up and down during manual and piston based compression. This acts to damp CPR motive force and impair blood flow. It also may add to CPR related movement artifact on imaging.

These problems with the current automated CPR devices in the cathlab render them inadequate for their intended purpose in the cathlab. It would be desirable to have an automated CPR device that overcame these limitations.

SUMMARY OF THE INVENTION

The method and devices described herein overcomes disadvantages of the prior art by providing a radiolucent cathlab vest-CPR device that can provide automated CPR and be synchronized with other cathlab equipment. Vest-CPR is more effective than manual CPR and existing automated devices, and can be more compatible with the cathlab. The pneumatic vest that is applied to the patient is completely radiolucent and will not interfere with imaging. It is associated with significantly less cardiac motion than sternal-based CPR. Unlike current automated CPR devices, it does not have a tendency to move out of the optimal location around the thorax. Because it spreads the motive force circumferentially, it is associated with significantly lower rates of thoracic skeletal and visceral organ injury. In its standard embodiment, it is free of a backboard and can be pre-positioned in high-risk patients. It can be integrated into the cathlab system so as to reduce thoracic and/or myocardial motion artifact. Integration of this device with other components of the cathlab allows for improved effectiveness of imaging, defibrillation, CPR, and hemodynamics. The integration of the cathlab imaging system with the CPR device allows removal of the CPR related cardiac motion artifact. Integration of this device with the contrast injector pump allows optimization of contrast media in the abnormal state of inadequate or absent spontaneous circulation. Integration of the CPR device with the defibrillator allows synchronization of the electrical countershock with the chest compressions.

BRIEF DESCRIPTION OF THE DRAWINGS

The invention description below refers to the accompanying drawings, of which.

DETAILED DESCRIPTION

Figure 1:
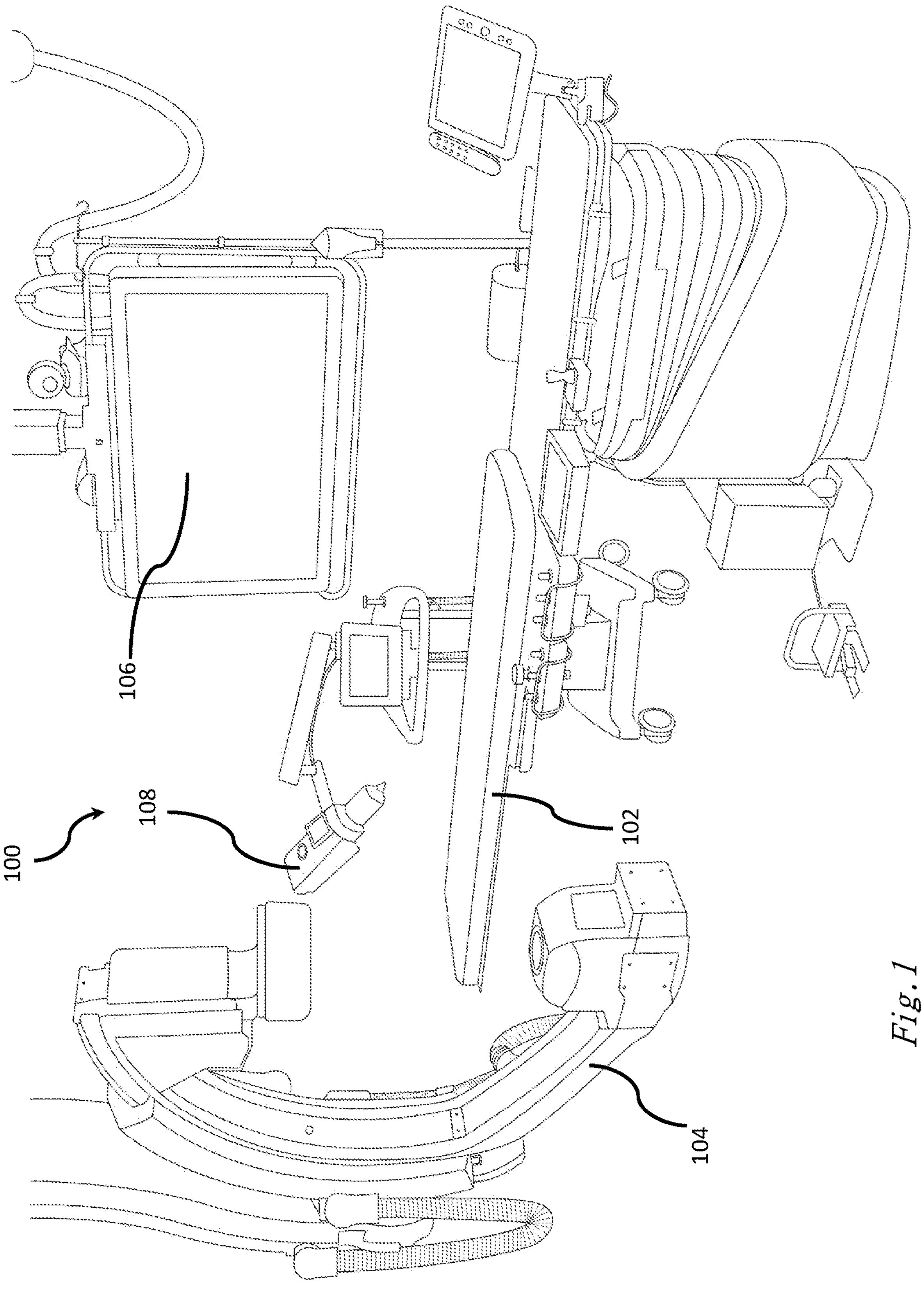
FIG. 1 is a perspective view of a typical Cathlab, showing various components, according to an illustrative embodiment.

The present devices and methods described herein overcome disadvantages of the prior art by providing a radiolucent vest-CPR device that can be synchronized with other cathlab equipment to create an integrated Cathlab and CPR system that can improve efficacy and patient outcomes. The method can integrate an automated CPR device and all major cathlab components that might be used during PCI in cardiac arrested patients to achieve both more effective resuscitation and more effective PCI.

Vest-CPR is more effective than manual CPR and existing automated devices Vest CPR can include application of circumferential constriction CPR using an inflatable or pneumatic vest, as taught in U.S. Pat. No. 10,772,793 to Paradis, titled MECHANICAL CARDIOPULMONARY RESUSCITATION COMBINING CIRCUMFERENTIAL CONSTRICTION AND ANTEROPOSTERIOR COMPRESSION OF THE CHEST, the entire disclosure of which is incorporated herein by reference, and U.S. Patent Publication No. 2021/0059900 to Halperin et al., titled DEVICES AND METHODS FOR ACTIVE DECOMPRESSION OF THE CHEST DURING CIRCUMFERENTIAL CONSTRICTION CARDIOPULMONARY RESUSCITATION, the entire disclosure of which is incorporated herein by reference. Vest CPR is not only more effective at creating forward blood flow, but also is intrinsically safer with respect to skeletal and visceral organ injury. Cathlab patients are often anticoagulated, and the injuries created by the existing automated CPR devices and manual CPR, or particularly concerning in patients who cannot properly form blood clots.

The vest CPR component that is applied to the patient can be completely radiolucent and will not interfere with imaging. The patient portion of vest CPR can be a fully enclosed pneumatic bladder made of materials such as ballistic nylon or radio welded polyurethane coated ballistic nylon.

When not inflating, the CPR vest can have a form factor that is completely flat, or nearly completely flat. It can thus be laid across the cathlab table beforehand and closed around the patient only when needed. It's presence, when not being utilized, causes no patient discomfort and no impact on cathlab procedures.

Vest CPR is associated with significantly less cardiac motion than sternal-based CPR techniques. In many cases, the cardiac arrest that supervenes a PCI is caused by occlusion of one or more coronary arteries. While CPR is needed to prevent irreversible brain injury after the occlusion has occurred, in most cases the PCI procedure should continue with the purpose of alleviating the coronary occlusion and reestablishing coronary blood flow. However, existing CPR techniques create a large degree of abnormal motion of the myocardium and other mediastinal structures. This cyclic anterior to posterior motion artifact interferes with the ability of the interventional cardiologist to delineate structures and continue with PCI procedures. Circumferential vest CPR does induce anterior to posterior motion of the precordium, but because it stabilizes the whole of the thorax circumferentially, abnormal cardiac motion is significantly reduced as compared to manual CPR or piston-type mechanical CPR.

Unlike, current automated CPR devices, vest CPR does not have a tendency to move out of its optimal location and orientation around the patient's thorax. Current automated devices often require that cathlab personnel direct their attention towards preventing movement of the piston device away from the mid sternum. This is not required with vest CPR. Vest CPR can also include use of multiple pneumatic bladders in different locations, and different bladders can be inflated separately or in combination with other bladders, as taught in U.S. Patent Publication No. 2019/0209428 to Paradis, titled METHODS AND DEVICES TO IMPROVE THE EFFICACY OF MECHANICAL CARDIOPULMONARY RESUSCITATION BY CHANGING THE POSITION OF CHEST COMPRESSION, the entire disclosure of which is incorporated herein by reference. This allows the location and/or direction of compressive force to be varied in a way that can maximize the effectiveness of CPR and/or maximize the effectiveness of cathlab procedures including imaging of the heart and coronary arteries.

Because it can spread the motive force circumferentially, vest CPR is associated with significantly lower rates of thoracic skeletal and visceral organ injury. This can be a significant advantage in a population of patients that are often anticoagulated.

Unlike existing automated CPR devices, vest CPR can be free of a backboard, and can be pre-positioned in high-risk patients. The backboards of existing automated CPR devices are relatively thick and cannot be pre-positioned as they would be uncomfortable to patients who are conscious or mildly sedated.

It has also been previously described that integration of defibrillation capabilities into a CPR device can improve the efficacy of defibrillation, as described in U.S. Pat. No. 11,253,713 to Paradis, titled INCORPORATION OF THE ELECTRODES FOR DEFIBRILLATION INTO THE PATIENT-FACING COMPONENTS OF AUTOMATED CARDIOPULMONARY RESUSCITATION SYSTEMS, the entire disclosure of which is incorporated herein by reference. Synchronization of defibrillation and chest compression are also described in U.S. Pat. No. 8,478,401 to Freeman, titled SYNCHRONIZATION OF DEFIBRILLATION AND CHEST COMPRESSIONS, the entire disclosure of which is incorporated herein by reference, and U.S. Pat. No. 7,645,247 to Paradis, titled NON-INVASIVE DEVICE FOR SYNCHRONIZING CHEST COMPRESSION AND VENTILATION PARAMETERS TO RESIDUAL MYOCARDIAL ACTIVITY DURING CAR- DIOPULMONARY RESUSCITATION, the entire disclosure of which is incorporated herein by reference.

Figure 2:
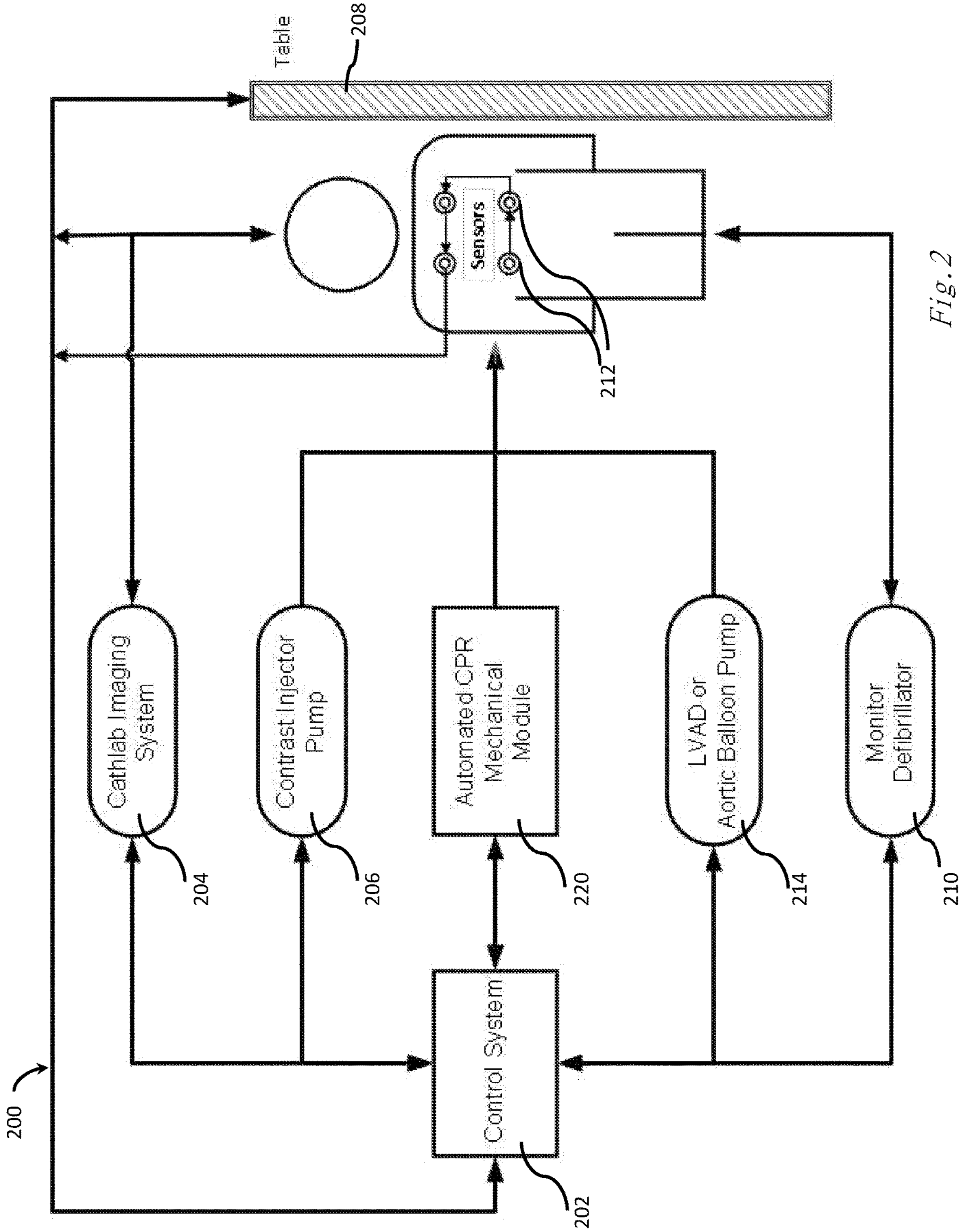
FIG. 2 is a schematic diagram of an integrated multimodal Cathlab and CPR system that can incorporate various components of a cathlab with an automated CPR system, according to an illustrative embodiment.

FIG. 2 is a schematic diagram of an integrated multimodal Cathlab and CPR system 200 that can incorporate various components of a cathlab with an automated CPR system, according to an illustrative embodiment. As used herein, the term multimodal system describes a system that integrates, coordinates, and/or synchronizes multiple treatment modalities together in the same system. As used herein, the term modality refers to each component of the integrated system, including, but not limited to, an imaging system, a contrast injector pump, a CPR vest, a defibrillator, and/' or other various components. Each of these components of the integrated multimodal system can be referred to as a modality. As described herein, a multimodal system integrating automated CPR with various cathlab components can include multiple modalities, including, but not limited to:

- a control system, or controller 202, which may be in the form of a computer or other processor, and may be a separate component or may be integrated into various other components of the cathlab;
- a cathlab imaging system 204, which can be in the form of a monoplane or biplane fluoroscopy CPR-T-arm, computerized tomography, or magnetic resonance imaging;
- a radio contrast injector pump 206;
- a controllable cathlab table for appropriate positioning of the patient within the imaging modality 208;
- a physiologic monitor that may include a defibrillator 210;
- patient sensors 212 that can include sensors for components of the electrocardiogram, ET-CO2, chest wall motion, or chest wall force; and/or an integrated left ventricular assist device, intravascular pump, or aortic balloon pump 214.

The controller 202 of the cathlab can be connected to, and can integrate with, the automated CPR device 220. Integration of the automated CPR device 220 with the other cathlab devices allows improved performance of multiple components, including:

- Integration with the cathlab imaging system 204 allows removal of the CPR related cardiac motion artifact;
- Integration with the contrast injector pump 206 allows optimal administration of contrast media in the abnormal state of spontaneous circulation being absent. By way of illustration, administration of contrast when the chest is being decompressed;
- The CPR device 220 can be controlled by the cathlab controller 202, which then allows the cathlab physicians to manually control the CPR device. Manual control of the mechanical CPR device allows operators to vary the rate and force while observing coronary flow. The characteristics of the CPR parameters, such as rate or force, can be optimized by a physician and/or by the control system 202.
- Integration of a defibrillator 210 with the cathlab equipment and/or CPR device 220 allows for countershock during the period of greatest efficacy, as described in U.S. Pat. No. 8,478,401, and synchronization with CPR during the pulseless electrical activity, as described in U.S. Pat. No. 7,645,247, the entire disclosures of which are incorporated herein by reference.
- Integration with physiologic monitoring sensors 212 allows use of measured biomarkers that can include ECG, ET-CO2 in algorithms to enhance function of the cathlab procedures and/or CPR in real time. In various embodiments, the sensors 212 that collect the measured biomarkers can be afferent components that provide data to the controller 202 as part of a closed loop control system.

Removal of Abnormal Cardiac Motion Caused by CPR

Image gating can be used for the removal of motion artifacts caused by predictable cyclic processes such as ventilation. When used for motion artifacts caused by respiratory motion, predictive respiratory gating can be implemented. In this approach the breathing pattern of the patient can be monitored and the data can be used to predict when motion will cease temporarily in the respiratory cycle, and the imaging system can start scanning automatically for this time duration.

Although vest CPR is associated with less abnormal cardiac motion than manual CPR and existing piston-type devices, vest CPR may still result in some abnormal motion of the cardiac structures. Integration of the imaging systems and CPR systems by means of a computer based controller can allow additional removal of the abnormal motion by means of gating. When image gating is used, the imaging display monitor would not show all portions of the CPR compression-decompression cycle. Instead, the user would be presented with real time imaging during that portion of the CPR cycle in which the mechanical device is in its release phase and all internal thoracic structures are in their native configuration. At end-release, the final fluoroscopic image would be retained on the monitor screen throughout the active constriction phase. Real time imaging can then re-initiate at the beginning of the next full release interval.

Figure 3:
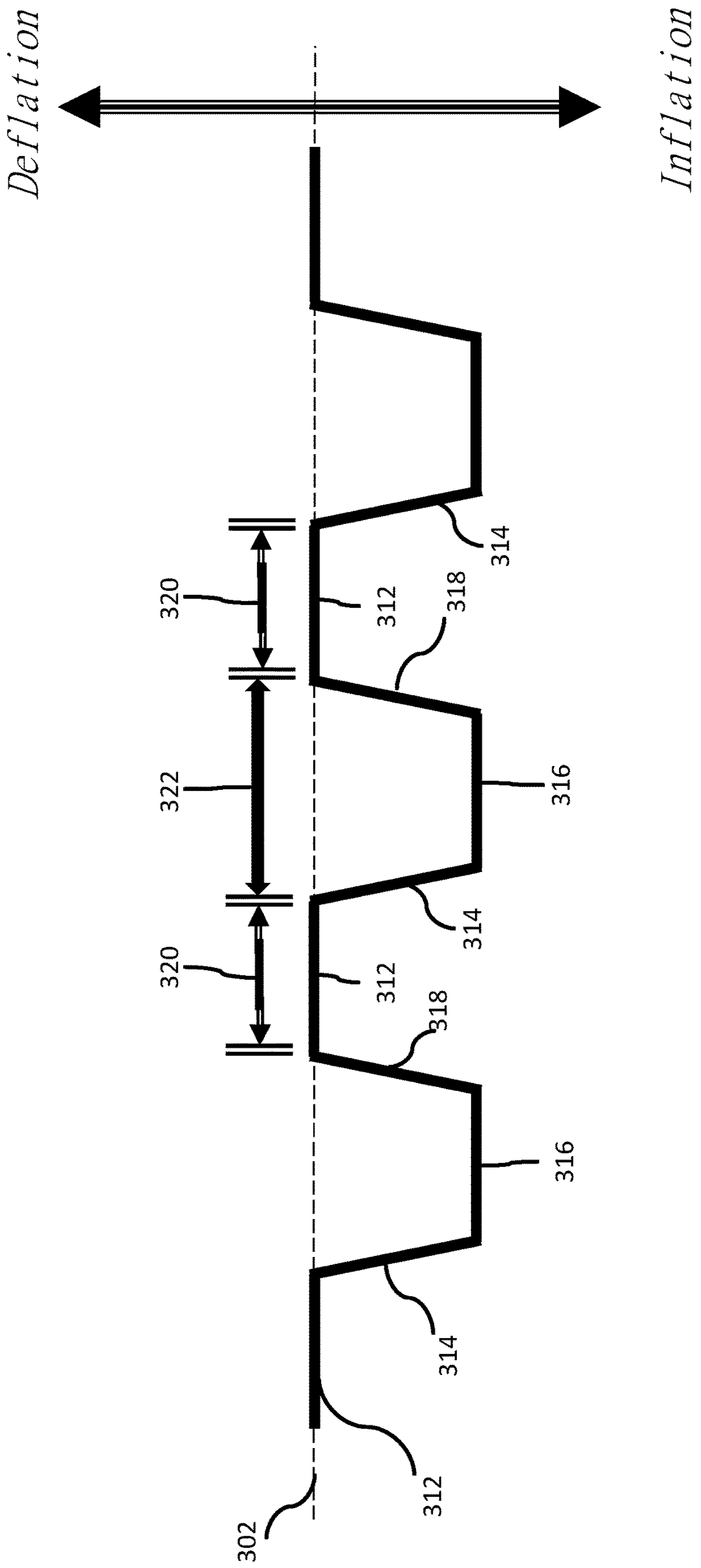
FIG. 3 is a chart showing the gating of imaging across CPR cycles, according to an illustrative embodiment.

FIG. 3 is a chart showing the gating of imaging across CPR cycles, according to an illustrative embodiment. Baseline 302 represents the state when the automated CPR device is not applying compression to the patient. Put another way, at baseline 302, the patient is at a normal anatomic, resting state, with all organs and internal structures in a normal position. At uncompressed stage 312 of the CPR cycle, the CPR machine is not applying any force or compression to the patient, and the patient is at a normal, resting state. At increasing compression stage 314, the CPR device is applying increasing compression to the patient in an effort to assist the movement of blood through the patient. At maximum compression stage 316, the CPR device has reached maximum compression, and is holding the compression in an effort to assist the movement of blood through the patient. In the case of a CPR machine with inflatable, or pneumatic, bladders, maximum compression stage 316 is the state of maximum inflation for the bladders. At releasing compression stage 318, the CPR device is releasing the compression on the patient until the cycle returns to uncompressed stage 312. With respect to vest CPR, deflation of the vest, or bladders of the vest, allows for the return to uncompressed stage 312. In various embodiments, the timing of the cycles can be the timing recommended by the American Heart Association for CPR. In various embodiments, the timing of the cycles can include 300 ms of uncompressed stage 312 and 300 ms of maximum compression stage 316 per cycle. In various embodiments, the timing of the cycle can be optimized by the controller and/or by the physician to improve the performance of CPR and/or improve the performance of the cathlab and cathlab imaging. In various embodiments, optimizing the timing of the CPR cycle can include adjusting the lengths of one or more of the uncompressed stage 312, increasing compression stage 314, maximum compression stage 316, and/or releasing compression stage 318.

The image gating system can allow the fluoroscopic image of the patient to be displayed on the monitor in real time during the imaging phase 320. Imaging phase 320 can be while the patient is in an uncompressed state. During the period of time between the imaging phases, also referred to as the non-imaging phase 322, a static image can be displayed on the monitor, showing and holding the last image taken during the imaging phase 320. In various embodiments, the non-imaging phase can include the increasing compression stage 314, the maximum compression stage 316, and the releasing compression stage 318. The gating system can provide live, real-time images while the patient is in an uncompressed state, and then hold the last image taken before compression starts, and then return to live, real-time imaging when the patient returns to an uncompressed state. The input signal for gating the imaging system may be obtained from the automated CPR device or from integrated accelerometers on the patient facing surface of the pneumatic vest.

Utilizing biomarkers of hemodynamics, and measures of abnormal cardiac motion from the imaging subsystem, it can be possible for the controller to adapt the pattern of CPR constrictions and compressions so as to maintain hemodynamics while minimizing abnormal cardiac motion. In various embodiments, this can be achieved in real time by using previously derived multivariable algorithms, and/or by using machine learning-based closed-loop control.

This coordination between the cathlab imaging system and the CPR system allows the physician to see the organs and internal structures of the patient without motion.

Synchronization of Radiocontrast Injection with CPR Chest Compressions

The forward movement through the patient's circulatory system of radiocontrast material deposited into the aortic root for cardiac catheterization during cardiac arrest is often impaired due to relatively low forward blood flow. Integration of the radiocontrast injection pump and CPR system by means of a computer-based controller can allow optimization of contrast movement into the coronary vasculature. Contrast injection can also be enhanced by synchronizing the injection of contrast material with CPR relaxation, such as releasing compression stage 318 and/or uncompressed stage 312, because the lower intrathoracic pressure may enhance injection.

Synchronization of Defibrillation and Thoracic Compression or Constriction

As noted above, defibrillation and CPR compressions can be synchronized. In the cathlab, the synchronization can be achieved automatically by integration of the cathlab CPR device and the defibrillator with the controller.

Synchronization of Aortic Balloon Counterpulsation and CPR

The cathlab is an ideal environment for the placement of an aortic counterpulsation balloon pump when cardiac arrest or cardiogenic shock occurs, such as the aortic counterpulsation balloon pump taught in U.S. Pat. No. 3,585,983 to Kantrowitz, titled CARDIAC ASSISTING PUMP, the entire disclosure of which is incorporated herein by reference. This aortic balloon pump can augment coronary flow. An automated CPR device can be synchronized with an aortic balloon pump so as to inflate the aortic balloon during each relaxation phase of the CPR thoracic constriction or compression, such as releasing compression stage 318 and/or uncompressed stage 312. This will act synergistically to enhance coronary flow, which happens during the relaxation phase of CPR.

Synchronization of Left Ventricular Assist Devices and CPR

It is possible to use left ventricular assist devices in the cathlab when cardiac arrest or cardiogenic shock occurs, such as the ventricular assist device taught in U.S. Pat. No. 7,841,976 to McBride et. al, titled HEART ASSIST DEVICE WITH EXPANDABLE IMPELLER PUMP. This ventricular assist device can augment coronary flow as well as cardiac output. Such devices can potentially function in a phasic pulsatile pattern. An automated CPR device can be synchronized with left ventricular assist devices functioning in a phasic pattern so as to synchronize CPR constrictions or compressions with the phasic pattern of the ventricular assist device and enhance systolic or diastolic blood flow. This will act synergistically to enhance coronary flow, cardiac output, or both.

During true cardiac arrest with CPR being applied, LVAD's could synchronize their pulsatile assist to cardiac output coincident with the compression-constriction phase of CPR and their venous return assist with CPR relaxation phase.

Circulatory Assist After Restoration of Spontaneous Hemodynamics

A circumferential constriction CPR vest may function as non-invasive left ventricular assist devices to enhance cardiac output, or coronary flow, after restoration of spontaneous circulation. This is achieved by synchronization vest constrictions with native cardiac function. Synchronization with systole may enhance overall cardiac output, as can be achieved invasively with pulsatile left ventricular assist devices. Synchronization with diastole may enhance coronary blood flow as is achieved invasively with aortic counterpulsation balloons.

Integrated CPR and Cathlab Device

By way of illustration, but not limitation, an exemplary version of this device or method may incorporate and integrate some or all of:

- A computer based controller receiving inputs from various subsystems and capable of controlling various subsystems;
- An automated CPR device providing chest compressions and constrictions to achieve hemodynamics during cardiac arrest;
- A fluoroscopic or tomographic imaging system;
- A display of images capable of being gated so as to minimize abnormal coronary motion caused by CPR chest constrictions or compressions;
- A radiocontrast injection pump;
- An aortic balloon counterpulsation pump;
- A left ventricular assist pump; and/or
- A defibrillator.

The failure to synchronize the equipment of the automated CPR with the equipment of the cath lab can lead to suboptimal imaging and suboptimal therapeutics. The automated CPR system can be connected/integrated to various cath lab devices, including but not limited to: imaging system, injector pumps, monitor/defibrillator, and the cath lab table. Inputs from the automated CPR system can be utilized by the cathlab imaging system to gait the imaging acquisition and display so as to minimize abnormal coronary artery motion. Inputs from the automated CPR system can be utilized by the cath lab imaging system to create images of the coronary arteries without CPR related motion.

Removal of CPR related abnormal coronary motion may be multimodal. Sensors on the patient-facing surface of the automated CPR system can measure chest wall motion or force. Outputs from the patient-facing sensors can be utilized by the automated CPR system to alter the characteristics of the chest compression, constriction, or release so as to minimize coronary artery motion while maintaining hemodynamics. Imaging data from the cath lab system can be provided to a control unit capable of adjusting the automated CPR system so as to minimize coronary artery motion while maintaining hemodynamics. The control unit can be connected to both the cath lab imaging system and the automated CPR system. The control unit can be capable of optimizing both the pattern of chest constriction or compression and imaging acquisition gating so as to minimize coronary artery motion seen on the monitor by the physician.

The controller can be connected to both the automated CPR device and the angiographic injector pump of the cath lab such that dye injection can be timed to the release phase of CPR. The ECG monitor and the automated CPR system can be interconnected for synchronized CPR.

Unlike manual and piston based CPR, circumferential constriction CPR does not cause movement of the patient table. There is no damping of CPR motive force or impairment of blood flow. Further, there is little or no CPR related movement artifact on imaging.

The automated CPR system can have a low-pressure/force setting for circulatory assist in hypotension. This assist can be synchronized with the ECG by way of connection between the ECG monitor and the automated CPR system. Connection between the automated CPR system and the aortic balloon pump system can allow synchronization between chest CPR constriction-relaxation and aortic balloon inflation-deflation. Connection between the automated CPR system and a left ventricular assist device can allow synchronization between chest CPR constriction-relaxation and left ventricular assist device pulsatile flow.

Figure 4:
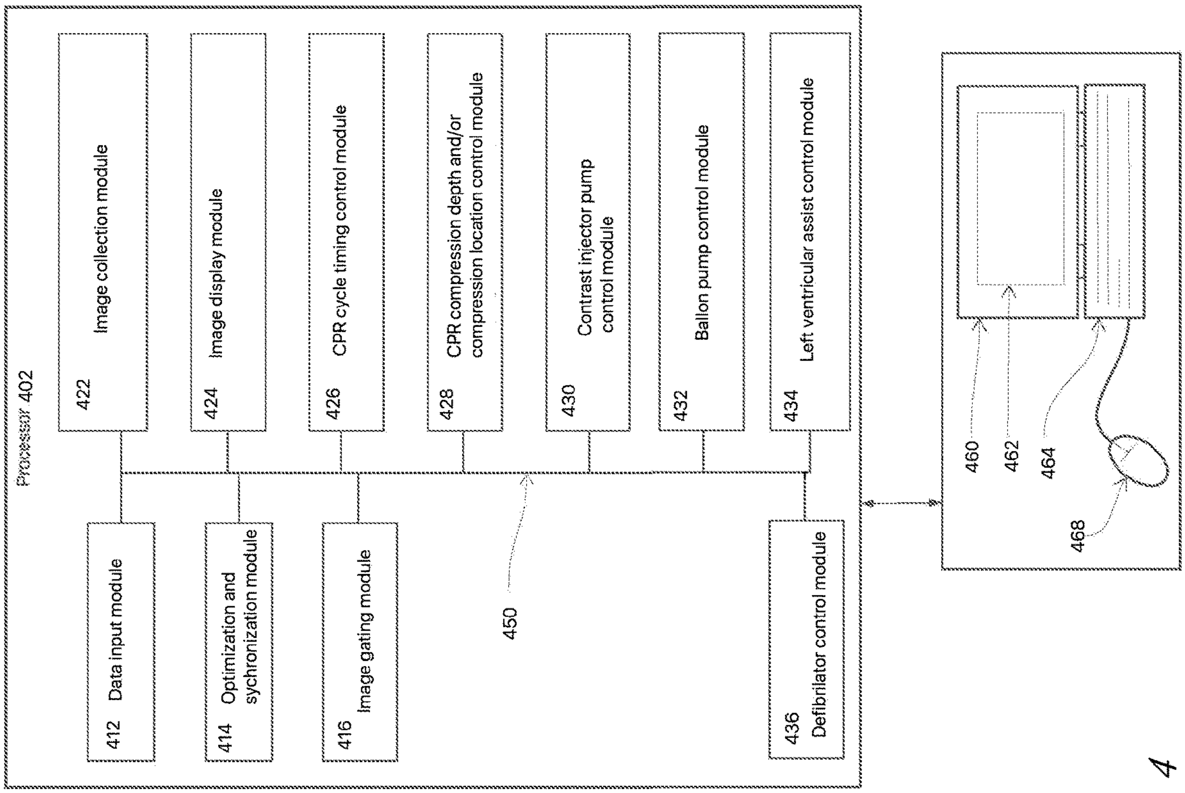
FIG. 4 is a schematic diagram showing an overview of a processing and controlling system for an integrated Cathlab and CPR system, according to an illustrative embodiment.

FIG. 4 is a schematic diagram showing an overview of a processing and controlling system for an integrated Cathlab and CPR system, according to an illustrative embodiment. An integrated Cathlab and CPR system can be controlled by a processor 402 that can include a plurality of modules, data inputs, and control outputs, and a user interface. The processor can be contained within a general purpose, or a dedicated, computing device 460, such as a PC, laptop, tablet or smartphone. In various embodiments, the computing device 460 can be built into, or incorporated within, a housing of the Cathlab or any of the various components. The computing device can include a user interface that can be a keyboard 464, mouse 466, touch screen or similar device, and a display 462 that can include a graphic user interface screen. In practice, a user can input instructions for a procedure through the user interface 464 into the processor 402. The programs and/or sub-programs can then process the instructions, collect measurements, and provide information to the various subsystems of the integrated cathlab and CPR system.

The processor unit 402 can include a data input module 412 and an optimization and synchronization module 414 that can be used by the processor to optimize the performance of the integrated cathlab and CPR system. The data input module 412 can input data collected from various sensors, meters, or other afferent components of the system, and the data input module 412 can input data collected from the CPR device, cathlab equipment, or other effector components that act on the patient. The optimization and synchronization module 424 can use the collected data to optimize and synchronize the various subsystems. The optimization and synchronization module 424 can synchronize various subsystems to work together to improve patient outcomes. By way of non-limiting example, the optimization and synchronization module 424 can coordinate the timing of the CPR compression and/or the depth of CPR compression with the image collection system and image gating module to produce a smooth image on the image display module that can be free of motion artifact. In various embodiments, the processor unit 402 can start with predetermined parameter values most likely to lead to the best treatment efficacy, and the optimization and synchronization module 424 can optimize various parameter values, such as CPR timing, CPR depth, CPR compression location, and image collection timing, in real-time based on data collected by the data input module 412. The control system can begin treatment with predetermined parameter values, and can then optimize in real time to improve treatment as the treatment is occurring by collecting biomarker measurements and/or physician inputs, and adjusting various subsystems in response to the collected data and/or physician inputs.

The processor unit 402 can include an image gating module 416 that can provide instructions to the image collection module 422 and/or image display module 424 so that the image displayed in the display monitor shows the patient in real time for the imaging phase of the CPR cycle, and during the non-imaging phase of the CPR cycle, shows a static image on the monitor, showing and holding the last image taken during the imaging phase. The image gating module can provide instructions to the image collection module and/or the image display module to provide live, real-time images while the patient is in an uncompressed state, and then hold the last image taken before compression starts, and then return to live, real-time imaging when the patient returns to an uncompressed state. In various embodiments, this can include instructing the image collection module to switch the image collection system on and off at the appropriate times in the CPR cycle. In various embodiments, this can include instructing the image display module to display live images during the imaging phase and to hold a static image during the non-imaging phase.

The processor unit 402 can include an image collection module 422 that can control the functions of the imaging subsystem, such as a fluoroscopy device. The processor unit 402 can include an image display module 424 that can control the functions of the image display subsystem, such as a monitor. The processor unit 402 can include a CPR cycle timing control module that can control the timing of the CPR compressions and the timing of the various stages of the CPR compressions. The processor unit 402 can include a CPR compression depth and/or CPR compression location control module 428. The CPR compression depth and/or CPR compression location control module 428 can control the depth of compression by controlling the level of inflation for the bladder(s) of the CPR vest. In various embodiments, the CPR compression depth and/or CPR compression location control module 428 can control the location of compression by controlling which bladders are inflated and/or how much each bladder is inflated. The processor unit 402 can include a contrast injector pump control module 430 that can control various parameters of contrast injection, including when the portions of contrast are injected, how much is injected when, when the saline is injected, etc. The processor unit 402 can include a balloon pump control module 432 that can control the functions of the balloon pump. The processor unit 402 can include left ventricular assist control module 434 that can control the functions of the left ventricular assist device. The processor unit 402 can include a bus 450.

As a non-limiting illustrative example, an embodiment of a multimodal integrated cardiac catheterization laboratory system to improve the outcome of cardiac arrest patients may have multiple modalities, including:

An automated CPR device that can have a traditional sternal piston-type mechanism, or a circumferential constriction CPR system, such as the one taught in U.S. Pat. No. 4,928,674 to Halperin, titled CARDIOPULMONARY RESUSCITATION AND ASSISTED CIRCULATION SYSTEM, the entire disclosure of which is incorporated herein by reference. This device may be connected to other components of the integrated system by cable or wireless connection.

The radiographic imaging system may be x-ray fluoroscopy, computerized tomography, magnetic resonance imaging and/or other imaging systems. The fluoroscopy can be either monoplane or biplane utilizing a traditional C-arm configuration. The imaging system can include various image-collecting components and an image display component. This device may be connected to other components of the integrated system by cable or wireless connection.

The control system adapted to integrate and synchronize the other components may incorporate one or more mechanisms to connect to and control the other components.

The control system can remove the CPR related movement artifact from the images of the myocardium and coronary arteries by means of image gating the radiographic imaging so as to retain the image acquired at the end of the end of the automated CPR release through the whole of the compression phase thereby removing CPR motion artifact. Thus, the operator could see only the images of the coronary artery, myocardium, and cardiac chambers during chest release, when they are in their native configuration.

The control system can control the integrated contrast injector pump, so as to synchronize the timing of the contrast injection such that it can inject contrast dye during the release phase of cardiopulmonary resuscitation. The increased intrathoracic pressure generated by CPR compression may act to impair radio contrast injection. This may be avoided if the injection occurs during the release phase. Additionally, coronary blood flow during CPR is greatest during the relaxation phase, and radio contrast injection during this interval can provide optimal images of the coronary anatomy. A particular optimal time of injection could be during the initial 100 milliseconds of CPR relaxation.

The control system can control an integrated aortic balloon pump such that during complete cardiac arrest, i.e. cardiac standstill, the balloon can be inflated in synchrony with the chest constriction or compression. This would act to enhance cardiac output. Deflation of the balloon in synchrony with CPR relaxation would enhance the venous return. Alternatively, inflation of the balloon during the relaxation phase of CPR may enhance coronary perfusion pressure and coronary artery blood flow. If, however, there is residual coordinated but inadequate cardiac contractions, as is described in U.S. Pat. No. 7,645,247, the entire disclosure of which is incorporated herein by reference, the balloon may be inflated in synchrony with the residual ventricular function, again, this would act to enhance cardiac output and venous return.

The control system would be capable of controlling an integrated left ventricular assist device such that during complete cardiac arrest, i.e. cardiac standstill, the pulsatile flow is in synchrony with the chest constriction or compression such that the expulsion of blood by the LVAD is during the compression phase of CPR. This would act to enhance cardiac output. Alternatively, expulsion of blood by the LVAD during the relaxation phase of CPR may enhance coronary perfusion pressure and coronary artery blood flow. If there is residual coordinated but inadequate cardiac contractions, as is described in U.S. Pat. No. 7,645,247, the entire disclosure of which is incorporated herein by reference, the pulsatile flow in synchrony with the residual ventricular function, again, this would act to enhance cardiac output.

The integrated cathlab and CPR system may incorporate motion, acceleration, or force sensors on patient facing surfaces of the device to measure one or both of chest wall motion or chest wall force. These data streams may be utilized by the control system as inputs to: 1) alter the pattern of chest constriction so as to minimize coronary artery motion, 2) time the injection of radiocontrast, 3) synchronize intravascular hemodynamic assist devices, and/or 4) gait the imaging system so as to minimize motion artifact.

The control system can receive data from the ECG monitor, so as to synchronize the CPR system, and/or one of the other components including balloon pumps or LVADS, with an organized ECG QRS, if it is present. An organized QRS on the ECG raises the possibility of retained ventricular function. Coordination and synchronization of the other modalities with this retained function may improve their efficacy, as is taught in U.S. Pat. No. 7,645,247.

Circumferential constriction CPR has the additional advantage that it can perform both CPR when patients are in cardiac arrest and ventricular assist when they are in cardiogenic shock. Circumferential constriction CPR devices provide CPR when the pneumatic force applied to the thorax is in the range of 4-6 pounds per square inch (PSI), and cardiac assist when the force is less than this range. The control system can apply CPR or cardiac assist based on data received from the physiologic monitor. Patients in cardiac arrest generally have characteristic ECGs, no detectable blood pressures, and ET-CO2 below 30 mmHG. Multivariable algorithms composed of these data streams can reliably and accurately separate cardiac arrest from cardiogenic shock. The control module can utilize such algorithms and then adjust the force of circumferential constriction to the appropriate level. Alternatively, operator input to the control device may allow selection of CPR or cardiac assist.

The control system can move the mechanized patient table such that the table acts to damp patient motion created by the cardiopulmonary resuscitation system. This may further act to remove CPR related movement artifact on the images. Sensors on or within the table can sense motion and the controller can then trigger actuators to damp or remove this motion.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. By way of non-limiting example, the system described herein may also coordinate with a ventilation system so that motion caused by artificial ventilation assistance can be controlled and/or gated so that the imaging of a patient is less affected by ventilation motion. Accordingly, this description is meant to be taken only by way of example, and not to otherwise limit the scope of this invention. Additionally, where the term "substantially" or "approximately" is employed with respect to a given measurement, value, or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Accordingly, this description is meant to be taken only by way of example, and not to otherwise limit the scope of this invention.

What is claimed is:

1. A multimodal integrated cardiac catheterization laboratory and CPR system comprising:

a radiographic imaging system comprising:

an image collecting system; and an image displaying system;

a pneumatic circumferential constriction cardiopulmonary resuscitation system having motion sensors on surfaces of the vest that are configured to be patient facing and configured to measure chest wall motion;

a radiocontrast injector pump;

a mechanized patient table;

an intravascular hemodynamic assist device;

a control system adapted to synchronize modalities such that:

the imaging and cardiopulmonary resuscitation systems are synchronized such that the image display system displays live images collected by the image collecting system during an uncompressed stage of CPR, and so that the imaging system displays a static image collected by the imaging collecting system during an increasing compression stage, a maximum compression stage, and a releasing compression stage of CPR;

the radiocontrast injector pump and cardiopulmonary resuscitation systems are synchronized such that the contrast injection occurs during the relaxation phase of the chest constrictions;

the mechanized patient table and cardiopulmonary resuscitation systems are synchronized such that the table acts to damp patient motion created by the cardiopulmonary resuscitation system; and the intravascular hemodynamic assist device and cardiopulmonary resuscitation systems are synchronized.

* * * * *